United States Patent
Giannuzzi et al.

(10) Patent No.: US 7,442,924 B2
(45) Date of Patent: Oct. 28, 2008

(54) REPETITIVE CIRCUMFERENTIAL MILLING FOR SAMPLE PREPARATION

(75) Inventors: Lucille A. Giannuzzi, Orlando, FL (US);
Paul Anzalone, Merrimack, NH (US);
Richard Young, Beaverton, OR (US);
Daniel W. Phifer, Jr., Chelsea, MA (US)

(73) Assignee: FEI, Company, Hillsboro, OR (US)

( * ) Notice: Subject to any disclaimer, the term of this patent is extended or adjusted under 35 U.S.C. 154(b) by 308 days.

(21) Appl. No.: 11/351,315

(22) Filed: Feb. 9, 2006

(65) Prior Publication Data

US 2006/0186336 A1 Aug. 24, 2006

Related U.S. Application Data

(60) Provisional application No. 60/655,327, filed on Feb. 23, 2005.

(51) Int. Cl.
*G01N 23/00* (2006.01)
*G21K 7/00* (2006.01)

(52) U.S. Cl. .......... 250/307; 250/304; 250/306; 250/309; 250/310; 250/251; 250/424; 250/441.11; 250/396 R; 250/492.21; 250/492.2; 250/492.22; 250/396; 430/5; 430/296; 428/141; 438/800; 216/2

(58) Field of Classification Search ........... 250/306, 250/307, 309, 310, 441.11, 396 R, 492.21, 250/492.2, 492.22, 396 ML, 440.11, 491.1, 250/304, 251, 424; 430/5, 296; 428/141; 438/800; 216/2
See application file for complete search history.

(56) References Cited

U.S. PATENT DOCUMENTS

| | | | |
|---|---|---|---|
| 4,936,968 A | | 6/1990 | Ohnishi et al. |
| 5,270,552 A | * | 12/1993 | Ohnishi et al. .......... 250/307 |
| 5,435,850 A | | 7/1995 | Rasmussen |
| 5,851,413 A | | 12/1998 | Casella et al. |
| 6,140,652 A | * | 10/2000 | Shlepr et al. ........ 250/440.11 |
| 6,420,722 B2 | | 7/2002 | Moore et al. |

(Continued)

OTHER PUBLICATIONS

Claves, S.R., et al., Using a FIB to investigate the 3d Morphology of B-AlFeSi Intermetallic Particles, Materials Forum, 2004, pp. 1334-1340, vol. 28, Institute of Materials Engineering, Australasia, Ltd.

(Continued)

*Primary Examiner*—Jack I Berman
*Assistant Examiner*—Meenakshi S Sahu
(74) *Attorney, Agent, or Firm*—Scheinberger & Griner, LLP; David Griner

(57) ABSTRACT

A method of sample extraction entails making multiple, overlapping cuts using a beam, such as a focused ion beam, to create a trench around a sample, and then undercutting the sample to free it. Because the sidewalls of the cut are not vertical, the overlapping cuts impinge on the sloping sidewalls formed by previous cuts. The high angle of incidence provides a greatly enhanced mill rate, so that making multiple overlapping cuts to produce a wide trench can requires less time than making a single, deep cut around the perimeter of a sample.

31 Claims, 5 Drawing Sheets

U.S. PATENT DOCUMENTS

| | | |
|---|---|---|
| 6,538,254 B1 | 3/2003 | Tomimatsu et al. |
| 6,570,170 B2 | 5/2003 | Moore |
| 6,664,552 B2 | 12/2003 | Shichi et al. |
| 6,781,125 B2 | 8/2004 | Tokuda et al. |
| 6,870,161 B2 | 3/2005 | Adachi et al. |
| 2002/0121614 A1 | 9/2002 | Moore |
| 2002/0166976 A1 | 11/2002 | Sugaya |
| 2004/0144924 A1 | 7/2004 | Asselbergs et al. |
| 2006/0000973 A1 | 1/2006 | Tappel |
| 2006/0017016 A1 | 1/2006 | Tappel |

OTHER PUBLICATIONS

Miller, M.K., et al., Strategies for fabricating atom probe specimens with a dual beam FIB, Ultramicroscopy (available online Nov. 20, 2004), 102 (2005), pp. 2878-298.

Tseng, A.A., Recent developments in micromilling using focused ion beam technology, J. Micromech Microeng., Jan. 14, 2004, pp. R15-R34, v. 14.

Tseng, A.A., Recent developments in micromilling using focused ion beam technology, J. Micromech Microeng., Jan. 14, 2004, pp. R-15-R34, v. 14.

* cited by examiner

REPETITIVE CIRCUMFERENTIAL MILLING FOR SAMPLE PREPARATION

This application claims priority from U.S. Provisional Application No. 60/655,327 filed on Feb. 23, 2005 which is hereby incorporated by reference.

TECHNICAL FIELD OF THE INVENTION

The present invention relates to methods for extracting microscopic samples from substrates for further analysis.

BACKGROUND OF THE INVENTION

Transmission electron microscopes (TEMs) allow observers to see extremely small features, on the order of nanometers. A TEM sample, however, must be sufficiently thin for electrons to pass through. TEM samples are typically between about 20 nm and 200 nm thick.

Several techniques are known for preparing TEM specimens. These techniques may involve either cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chuck" or large sample that requires additional thinning before observation. In addition, these "lift-out" specimens may also be directly analyzed by other analytical tools, other than TEM.

For example, U.S. Pat. No. 5,270,552 to Ohnishi et al. describes using a focused ion beam to extract a sample by first milling a rectangular hole next to an area of interest, and then directing the beam into the sidewall of the rectangle to cut a "floor" under an area of interest, the floor being nearly parallel to the substrate surface. The ion beam then partially cuts around the circumference of the area of interest, and a probe is attached to the sample to be extracted. After the probe is attached, the remainder of the circumference is cut with the ion beam, and the sample, including the area of interest, is removed by the probe to which it has been attached.

Another focused ion beam technique is described in U.S. Pat. No. 6,570,170 to Moore, which describes extracting out a sample by making a "U"-shaped cut and then cutting the sample at an angle from the missing side of the "U" to undercut and free the sample. After the sample is freed, a probe is attached to the sample and it is lifted out.

In one technique that creates a thin sample requiring minimal additional processing before TEM observation, a focused ion beam cuts two adjacent rectangles on a substrate, the remaining material between the two rectangles forming a thin vertical wafer that includes an area of interest. A U-shaped cut is made at an angle partially along the perimeter of the wafer, leaving the wafer hanging by a tab on either side at the top of wafer. A probe is connected to the sample, and then the tabs are cut using the focused ion beam, freeing the sample.

All of these methods are time consuming. As more and more TEM samples are required to monitor nanofabrication processes, a more efficient process is needed for sample extraction.

SUMMARY OF THE INVENTION

An object of the invention is to provide an efficient method for extracting a sample from a substrate.

The invention entails making at least two overlapping perimeter cuts around an area of interest. The first perimeter cut can be made rapidly because it does not need to mill to the full depth of the sample to be extracted. Because the beam creates a sloping sidewall and because the subsequent cuts overlap the previous cuts, the beam in subsequent cuts impacts the sidewall at a relatively large angle of incidence, close to 89 degrees in some embodiments. The large angle of incidence greatly increases the milling rate, so that a sample can be freed around a perimeter in greatly reduced time. An additional cut under the area of interest frees the sample. A probe can be attached before or after the sample is freed.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Preferred embodiments of the present invention are directed to methods and an apparatus for efficiently extracting microscopic samples from substrates. In a preferred embodiment of the present invention, a sample is extracted by making multiple, overlapping cuts using a beam, such as a focused ion beam, to create a trench around a sample, and then undercutting the sample to free it.

As discussed in greater detail below, up to a point, the sputter yield increases as beam incidence angle increases (although yield drops sharply as the incidence angle approaches 90°). The present invention takes advantage of the relationship between incidence angle and milling rate by employing a milling algorithm that maximizes beam incidence angles during milling. The milling beam is used to make a series of overlapping circumferential cuts around the object of interest. For each successive cut, the beam position overlaps a previous edge position extending from the outer diameter to an inner diameter toward the region of interest. As a result, after the first cut, the ion beam always mills on an edge or specimen sidewall produced by a previous cut. The increased incidence angle resulting from milling on a sidewall increases the sputter yield (i.e., throughput) and yields a deeper trench toward the region of interest. After the circumferential milling has been completed, the sample section (including the region of interest) is left standing in a trench of a desired depth, freed on all sides except the bottom. The sample can then be freed on the bottom by directing the milling beam at an angle so as to undercut the freestanding sample and totally releasing it from the substrate material. Once the sample is cut free, a probe can be attached to the sample. The sample can then be lifted-out and manipulated to a sample grid or holder, it can be further milled for analysis, or it can be directly analyzed.

As referred to herein, the term "circumferential" is not limited to circular shapes, but is used to mean a closed curve of any desired shape extending around an object of interest. Skilled persons will recognize that the shape of the beam path during the circumferential cuts will define the shape of the sample that will ultimately be extracted. A series of circumferential cuts could be made such that the sample left standing will be of any desired shape (e.g., circle, oval, square, triangle, octagon, freeform, polygon, etc.). Likewise, the use of the term "diameter" is not limited to circular shapes but is used to refer to the distance across a perimeter of a circumferential cut of any shape.

Figure 1:
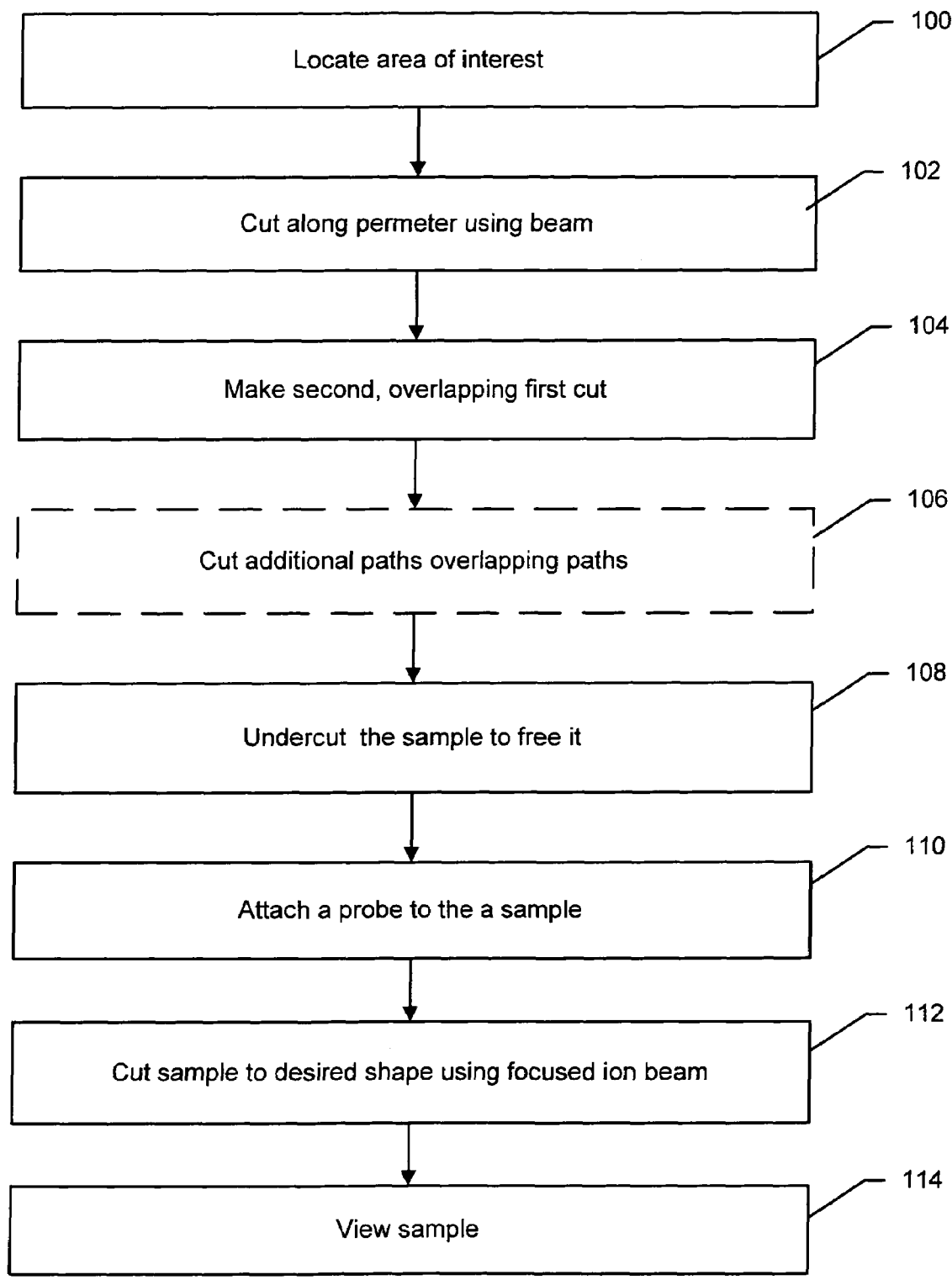
FIG. 1 is a flow chart showing the steps of a preferred embodiment of the present invention.

FIG. 1 is a flowchart showing the steps of a preferred embodiment of the invention for extracting a sample, including a region of interest, from a substrate without damaging the substrate away from the sample area. For example, if the substrate were a semiconductor wafer on which multiple integrated circuits are being fabricated, the sample could be extracted from one circuit without damaging the remaining circuits.

In step 100, the area of interest may be identified, for example, using a scanning electron microscope or using ion imaging via a focused ion beam microscope. A sample section to be extracted and which includes the area of interest is then defined. Step 102 shows that a first cut is made around a perimeter surrounding the sample section to be removed, but spaced away from the region of interest to allow additional cuts described below without damaging the region of interest. The beam could traverse, for example, a circle, rectangle, or other regular or irregular shape on the work piece surface.

Figure 2A:
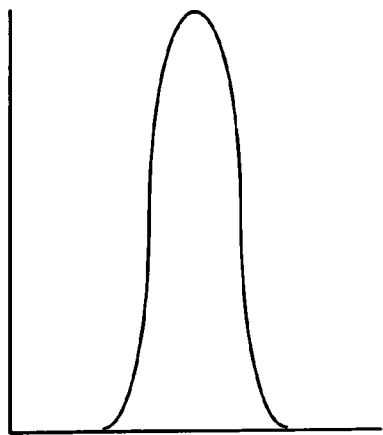
FIG. 2A shows an illustrative, not to scale, Gaussian current density distribution of a typical focused ion beam system.
Figure 2B:
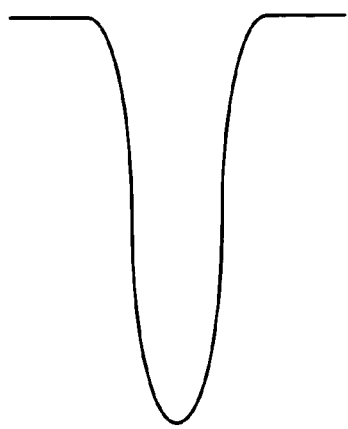
FIG. 2B shows a hole milled by a beam having the current density distribution shown in FIG. 2A

Although much of the following description is directed toward the use of FIB milling, the milling beam could comprise, for example, an electron beam, a laser beam, or a focused or shaped ion beam, for example, from a liquid metal ion source or a plasma ion source, or any other charged particle beam. A preferred embodiment uses a gallium liquid metal ion source to produce a beam of gallium ions focused to a sub-micrometer spot. Such focused ion beam systems are commercially available, for example, from FEI Company, the assignee of the present application. The beam preferably has a current density profile in which the current or energy density tapers off away from the center of the beam. For example, a focused ion beam system typically has a circularly symmetric, substantially Gaussian current density distribution, as illustrated in FIG. 2A, which shows a graph of ion current density versus position along a radial axis. Because there are more ions in the center of the beam and less on the edges, the "hole" produced by the beam is deeper in the middle. FIG. 2B shows the shape of a hole that would be milled by a stationary beam having the shape shown in FIG. 2A. As is well-known in the art, a moving beam would mill a "cut" or trench with the same general transverse cross-section as shown in FIG. 2B.

Figure 3A:
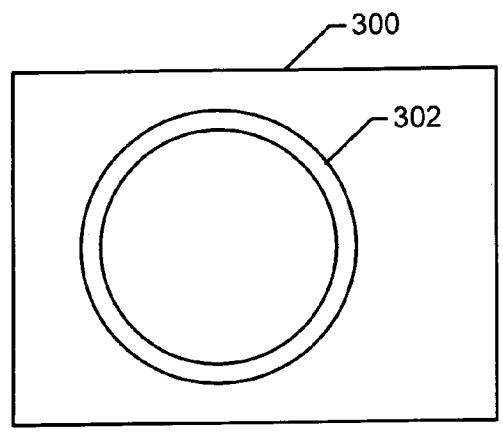
FIG. 3A shows a top view of a cylindrical hole milled as a first cut made in accordance with a preferred embodiment of the invention.
Figure 3B:
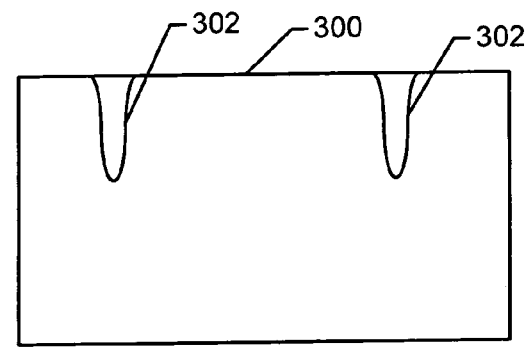
FIG. 3B shows a cross-sectional view of the hole of FIG. 3A.

FIG. 3A shows a top view of a substrate 300 in which a first cut 302 was made in step 102 and FIG. 3B shows a cross section of the first cut. FIG. 3B shows that the cut has sloping sidewalls due to the non-uniform, in this case Gaussian, current density profile of the beam. Because there are more ions in the center of the beam and less on the edges, the hole milled by the beam has is deeper in the middle. The shape of the cut is related to the inverse of the beam current density profile.

In step 104, the ion beam cut makes a second, overlapping cut. The second cut has the same shape as the first cut, but the second cut is offset, preferably toward the area of interest, and overlaps the first cut. Because the second cut overlaps the first cut, the ions in the beam during the second cut impinge on the sloping sidewalls of the first cut. In the case of circular cuts, the second cut has a slightly smaller diameter than the first cut so that the cuts form concentric circles of diminishing diameter. In the case of non-circular cuts, the ion beam will preferably be directed so that the ions in the beam impact the sidewall of the first cut closest to the area of interest (the inner sidewall). In some embodiments, the angle of incidence for the ions in the second cut can be close to 89 degrees (with respect to normal incidence), even though the beam axis continues to be normal to the surface of substrate 300.

Figure 4:
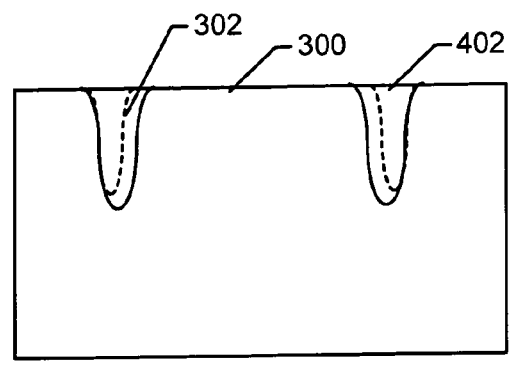
FIG. 4 shows a cross sectional of the hole of FIG. 3B after a second, overlapping cut is made.

The rate at which an ion beam removes material from a work piece, that is, the milling rate, depends upon the beam's angle of incidence, that is, the angle at which the ions impact the surface. Ions impacting the surface at a steep angle remove significantly-more material than ions impacting perpendicular to a surface. At a high angle of incidence, it is estimated that the milling rate can increase ten fold. Thus, for a given target, the sputter rate, and therefore specimen preparation throughput, will increase when milling with the ion beam close to parallel to a specimen edge rather than milling with the beam perpendicular to a target surface. The present invention takes advantage of the relationship between incidence angle and milling rate by scripting a set of circumferential milling beam cuts such that each beam position overlaps a previous edge position extending from the outer diameter to an inner diameter toward the region of interest using just one aperture setting (i.e., 20 nA). Because the ions of the second cut impact the sidewalls of the first cut, the incidence angle is higher and the second cut removes material much faster than the first cut. Because of the faster milling rate and the overlap, the second cut is deeper than the first cut, even if processing parameters (beam energy, current, and current density) remain the same. FIG. 4 shows the shape of the hole 402 after the second cut, superimposed on an image of the first cut 302 shown in dashed lines.

In most cases, several additional circumferential cuts will be performed in optional step 106, each cut moving inward toward the region of interest. In the case of circular cuts, each successive cut will preferably have a slightly smaller diameter than the previous cut so that the cuts form a series of concentric circles of diminishing diameter. The amount of offset between successive cuts will preferably be less than the ion beam spot size (diameter) so that (after the first cut is completed) most of the ions in the beam will impinge on the sloping sidewalls of the previous cut resulting in higher incidence angles.

Figure 5:
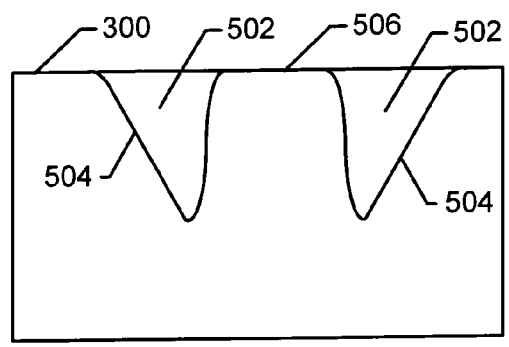
FIG. 5 a cross section of a work piece after several overlapping cuts have been made and the sample is freed around its perimeter.
Figure 6:
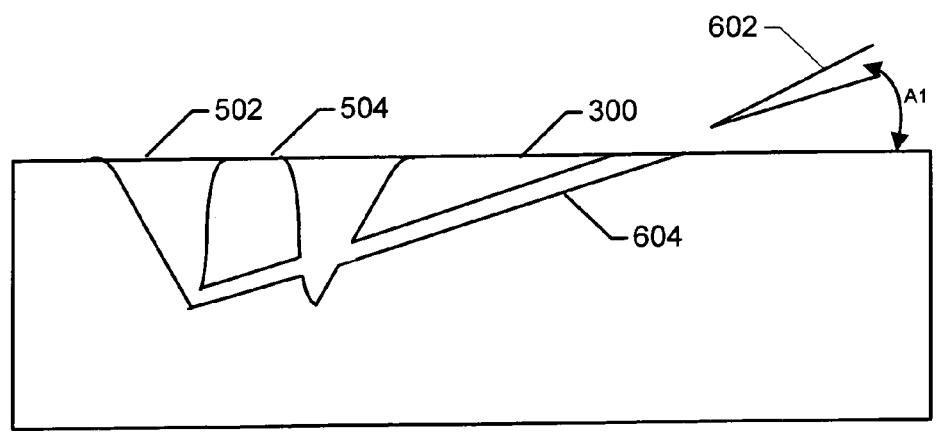
FIG. 6 shows the sample of FIG. 5 freed from the substrate by an angled cut.

FIG. 5 shows a cross section of the substrate resulting from multiple overlapping cuts. Skilled persons will recognize that what is referred to as single cut, such as the cut in step 102 or 104, is typically a thin annular cut made by the ion beam moving in a series of circular paths, each path having a successively smaller diameter, and then repeating the circles within the annulus multiple times before moving on to the next cut. Thus, the actual process of one preferred embodiment includes moving a beam multiple times in a series of circular paths of decreasing diameter within an annulus and then repeating the process on the next annulus, contiguous and concentric with the previous annulus but closer to the sample, that is, having a smaller diameter. At least two and preferably more than 5 and more preferably around 10 or more than 10 annuluses are milled to create the trench before the sample is undercut. Alternatively, steps 102, 104, and 106 can be repeated any number of times to deepen the previously milled cuts.

Further, while referred to as different cuts for ease of explanation, the "first cut," "second cut," and "subsequent cuts" discussed herein comprise circumferential cuts that are preferably performed as a single operation, and can be thought of as a single cut. No changes in angle or beam parameters (such as beam diameter, beam energy, current, or current density) are required, so the sample is isolated from all sides except the bottom in a single operation. A user can specify an area of interest or a trench to be milled, and the trench can be milled rapidly.

Because the first cut does not need to mill to the entire depth of the sample, the first cut can be relatively shallow compared to the prior art and can performed much more quickly than in prior art techniques that require the entire thickness of the sample to be milled to the required depth with the ion beam at a perpendicular angle of incidence. Each subsequent cut is deeper than the previous cut (because each subsequent cut impacts the sidewall at a large angle of incidence) and the sidewall is longer for each subsequent cut. FIG. 5 shows that the trench 502 has sloped sidewalls 504, with the portion of the trench that was milled last, that is, the portion nearest a sample 506, being significantly deeper that the part of the trench milled, first, with the trench in between getting progressively deeper toward the center.

The depth of the trench increases toward the sample such that the trench is sufficiently deep to free a sample that contains the area of interest by an undercut. The trench is sufficiently wide such that there is reduced opportunity for sputtered material to redeposit between the trench walls and the sample, potentially reattaching the sample. The depth and width of the trench and the number of passes with the ion beam will depend upon the size of the sample being extracted. In some embodiments, the width of the trench is greater than the one tenth the width of the sample remaining in the center of the trench. In other embodiments, the trench width is preferably greater than ⅓ the sample width, greater than ½ the sample width, greater than 1½ the sample width, or greater than the width of the sample. The combination of the pillar and bowl structure that results from the circumferential milling reduces the chance of the sample falling over or out of the cut area when it is freed from the substrate.

Figure 7:
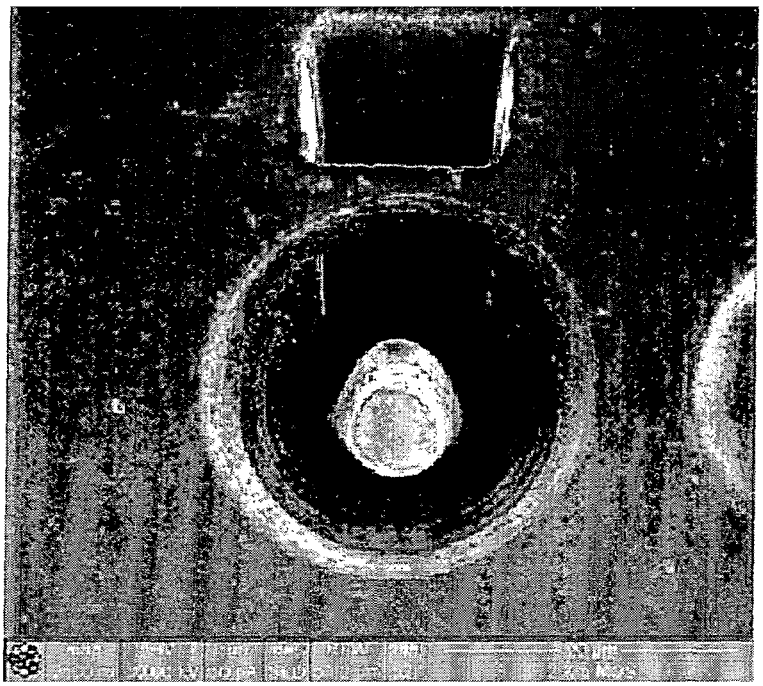
FIG. 7 is a photomicrograph of a work piece and sample processed in accordance with the invention.
Figure 8:
FIG. 8 is a photomicrograph of the extracted sample positioned onto a sample grid.

After milling completely around the circumference multiple times, the sample is left standing in a trench, freed on all sides except the bottom, and then the sample can then be freed by undercutting. In step 108, an ion beam is directed to the surface at an angle, A1, preferably between 10 degrees and 80 degrees, to undercut a sample, freeing it from the substrate as shown in FIG. 7. This angled hole can be rectangular or any other shape. Depending on the depth of the circumferential trench and its outer diameter, the undercut can be started either outside or inside the trench diameter. In the illustrated embodiment, the ion beam used to mill the circumferential trench is directed at an angle normal to the substrate surface (i.e., 90 degrees between the beam and the surface) while the undercutting beam is directed at a more acute angle with respect to the surface. Skilled persons will recognize that, in order to cut underneath the sample, the angle between the undercutting ion beam and the surface will need to be less than the angle between the surface and the beam used to mill the circumferential trench.

In step 110, a probe is attached to the freed sample. The probe can be attached, for example, using ion beam deposition, electron beam deposition, electrostatic attraction, mechanical gripping, or any other method. The probe can be a component of a micromanipulator tool allowing the probe (and the attached sample) to be positioned by way of the micromanipulator, as is well known in the art. In step 112, the extracted sample is shaped or thinned, preferably by polishing or by using a focused ion beam. In some embodiments of the present invention, the sample can be manipulated to a sample grid or holder prior to "final" thinning. After the sample is thinned, it is viewed in a transmission electron microscope or other analytical tool in step 114.

In another embodiment of the present invention, after the circumferential milling (but before the sample is undercut), the center portion of the specimen (the free-standing sample) can be polished or FIB milled to a desired shape or thickness. Then the sample can be tilted and undercut free, and/or it can be removed from the chamber system to an ex-situ manipulator station where the specimen can be lifted-out and manipulated for future analysis as necessary.

In many embodiments, all cuts can be performed using a single beam current, for example, a 20 nA beam current using beam energies that are readily available with many commercial FIB instruments (e.g., 10's of keV), with a dwell time and overlap that is typically used for FIB milling of Si. While preferred process parameters are described, skilled persons will understand that the preferred process parameters will vary with the size and shape of the sample and the material of the substrate. Skilled persons will be able to readily determine suitable process parameters for extracting samples in different applications.

The invention provides several advantages over the prior art. In many embodiments, the method requires only two cutting steps, with only a single reorientation of the sample and beam throughout the process.

In some embodiments, the invention produces a sample that is thicker on the bottom, which makes the sample tend to remain upright in the trench, facilitating attachment of the probe. The bowl-shaped trench reduces the probability of the sample falling out of the trench when it is freed.

In embodiments in which the subsequent cuts progress inwardly toward the sample, the redeposition of sputtered material deposits primarily on the substrate walls and not on the sample (because it is constantly being milled) so little or no material is redeposited onto the sample itself. This type of milling pattern also reduces redeposition artifacts that may cause sputtered material to close up trenches or holes already milled. In the prior art, a relatively thin line is typically cut partially, but not completely, around the diameter. Material sputtered during the undercutting operation tends to redeposit into the relatively thin cut, resulting in bridging by redeposition, which reattaches the sample to the substrate. Additional ion beam cuts normal to the surface are then required to remove the sputtered material and re-free the sample. The extra cuts require the time-consuming operations of changing the angle of the beam relative to the sample by tilting the stage and realigning the beam to make the additional cut(s). In contrast, the relatively wide trench produced in embodiments of the present invention reduces the likelihood of redeposition bridging during step 108.

The technique of the present invention is faster than most prior art methods and better facilitates automation because the vertical cuts can be made continuously without stopping, that is, going around the perimeter repeatedly, rather than milling part way and then performing other operations, as in the prior art. Because the ion beam impinges on the side walls in subsequent cuts, the time required to free a plug is significantly less that the time required when a single cut is made, even though multiple circumferential passes are made with the beam. In tests, the present method has been shown to be significantly faster than the prior art methods. Although a circumferential trench could also be milled using a traditional raster pattern, such a trench would be milled at a uniform depth. By milling in a circular fashion from outer to inner diameter, the position defined by the inner diameter will be the deepest. Since the material at the outer periphery of the circle need not be as deep as the region defined by the inner circle diameter, the time to mill is shorter.

Figure 9:
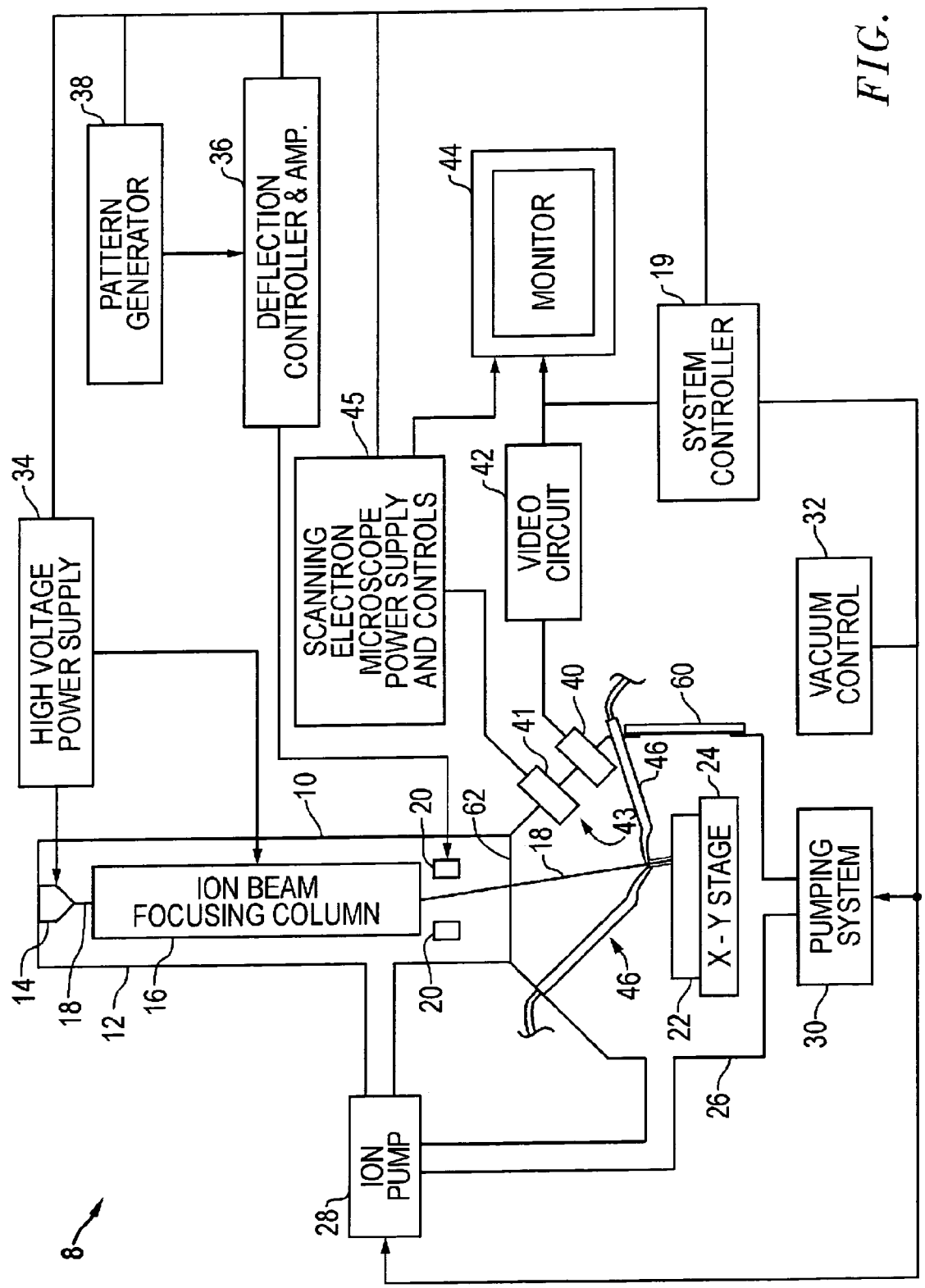
FIG. 9 shows a focused ion beam system suitable for implementing the present invention.

FIG. 9 shows a typical beam system, focused ion beam system 10, suitable for practicing the present invention. Focused ion beam system 10 includes an evacuated envelope 11 having an upper neck portion 12 within which are located a liquid metal ion source 14 and a focusing column 16 including extractor electrodes and an electrostatic optical system. Other types of ion sources, such as multicusp or other plasma sources, and other optical columns, such as shaped beam columns, could also be used, as well as electron beam and laser system.

An ion beam 18 passes from source 14 through-column 16 and between electrostatic deflection means schematically indicated at 20 toward sample 22, which comprises, for example, a semiconductor device positioned on movable X-Y stage 24 within lower chamber 26. A system controller 19 controls the operations of the various parts of system 10. Through system controller 19, a user can control beam 18 to be scanned in a desired manner through commands entered into a conventional user interface (not shown). Alternatively, controller 19 may control system 10 in accordance with programmed instructions.

For example, a user can delineate a region of interest on a display screen using a pointing device, and then the system could automatically perform the steps described in FIG. 1 to extract a sample. In some embodiments, system 10 incorporated image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

An ion pump 28 is employed for evacuating neck portion 12. The chamber 26 is evacuated with turbomolecular and mechanical pumping system 30 under the control of vacuum controller 32. The vacuum system provides within chamber 26 a vacuum of between approximately $1 \times 10^{-7}$ Torr (1×10E-7) and $5 \times 10^4$ Torr (5×10E-4). If an etch assisting, an etch retarding gas, or a deposition precursor gas is used, the chamber background pressure may rise, typically to about $1 \times 10^{-5}$ Torr.

High voltage power supply 34 is connected to liquid metal ion source 14 as well as to appropriate electrodes in focusing column 16 for forming an approximately 1 keV to 60 keV ion beam 18 and directing the same downwardly. Deflection controller and amplifier 36, operated in accordance with a prescribed pattern provided by pattern generator 38, is coupled to deflection plates 20 whereby beam 18 may be controlled manually or automatically to trace out a corresponding pattern on the upper surface of sample 22. In some systems the deflection plates are placed before the final lens, as is well known in the art. Beam blanking electrodes 70 cause beam 18 to impact onto blanking aperture 72 instead of target 22 when blanking controller 76 applies a blanking voltage to blanking electrode 70.

The source 14 typically provides a metal ion beam of gallium. The source typically is capable of being focused into a sub one-tenth micrometer wide beam at sample 22 for either modifying the sample 22 by ion milling, enhanced etch, material deposition, or for the purpose of imaging the sample 22. A charged particle detector 40, such as an Everhart Thornley or multi-channel plate, used for detecting secondary ion or electron emission is connected to a frequency sensitive amplifier, such as a lock-in amplifier 80, and a video circuit 42, the latter supplying drive for video monitor 44 also receiving deflection signals from controller 36.

The location of charged particle detector 40 within chamber 26 can vary in different embodiments. For example, a charged particle detector 40 can be coaxial with the ion beam and include a hole for allowing the ion beam to pass. In other embodiments, secondary particles can be collected through a final lens and then diverted off axis for collection. A scanning electron microscope 41, along with its power supply and controls 45, are optionally provided with the FIB system 10.

A gas delivery system 46 extends into lower chamber 26 for introducing and directing a gaseous vapor toward sample 22. U.S. Pat. No. 5,851,413 to Casella et al. for "Gas Delivery Systems For Particle Beam Processing," assigned to the assignee of the present invention, describes a suitable fluid delivery system 46. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A door 60 is opened for inserting sample 22 onto stage 24, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam column 16 for energizing and focusing ion beam 18. When it strikes sample 22, material is sputtered, that is physically ejected, from the sample. Alternatively, ion beam 18 can decompose a precursor gas to deposit a material. Focused ion beam systems are commercially available, for example, from FEI Company, Hillsboro, Oreg., the assignee of the present application. While an example of useable hardware is provided above, the invention is not limited to being implemented in any particular type of hardware.

While the embodiment described uses a focused ion beam, the invention is not limited to any particular type of beam and could be implemented for different materials using an electron beam with a chemical etchant, a laser beam, or other beam, or a combination of one or more said beams. Instead of using a focused beam, it is possible to use a shaped beam. The ion beam processing can be used with or without an etch-enhancing gas.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of extracting a microscopic sample from a substrate, comprising:
   directing an ion beam at a substantially normal angle to the substrate surface along a first path, said first path defining a substantially complete perimeter around a sample, to produce a trench in the substrate;
   directing the ion beam at a substantially normal angle to the substrate surface along a second path, the second path defining a substantially complete perimeter around the sample and overlapping but offset from the first path essentially along the entire perimeter to enlarge the trench around the sample; and
   directing the ion beam at a substantially non-normal angle to the substrate to undercut the sample and free the sample from the substrate.

2. The method of claim 1 further comprising attaching a probe to the sample.

3. The method of claim 2 in which attaching a probe to the sample includes attaching a probe to the sample after the directing the ion beam from an angle to intersect the gap to free the sample.

4. The method of claim 1 in which:
   directing an ion beam normal to the substrate includes directing a beam having a shape in which the current density decreases in the direction of outer diameter of the beam to make a cut having sloping sidewalls; and
   directing the ion beam normal to the substrate surface along a second path, inward of an overlapping the first path including directing the ion beam so that at least a portion of the ion beam impacts on the sloping sidewalls.

5. The method of claim 1 in which:
   directing an ion beam normal to the substrate surface includes directing an ion beam in a first circular path; and
   directing the ion beam along a second path includes directing the ion beam along a second circular path, the second circular path having a radius essentially concentric with the first circular path.

6. A method of extracting a microscopic sample from a substrate, the method comprising:
   directing a beam in a path to perform a series of overlapping cuts completely around the perimeter of a region of intrest containing a sample to be extracted and moving progressively toward the sample to be extracted to produce a trench around the sample, a portion of the trench becoming deeper in the direction toward the sample;
   severing the base of the sample; and
   removing the sample.

7. The method of claim 6 in which directing a beam in a path to perform a series of overlapping cuts moving progressively toward a sample including directing a focused ion beam.

8. A method of extracting a microscopic sample, the method comprising:
   cutting a trench essentially completely around an area of interest including the sample by beam milling around the perimeter of the sample in a at least one continuous pass so that the sample is essentially freed on all sides except the bottom; and
   undercutting the sample to free it from the substrate.

9. The method of claim 8 in which the cutting a trench includes making multiple offset, overlapping passes with a focused ion beam.

10. The method of claim 8 in which the cutting a trench includes moving a focused ion beam continuously around the perimeter of the sample making multiple offset, overlapping cuts without changing the beam angle, energy, current, current density, or diameter.

11. The method of claim 10 in which undercutting the sample to free it from the substrate comprises reducing the angle between the beam and the substrate, directing the beam at the base of the sample, milling away substrate material until the sample is freed from the substrate.

12. The method of claim 8 in which the cutting a trench includes cutting a trench that is wider than the sample.

13. The method of claim 8 in which the bottom of the trench becomes progressively deeper toward the sample.

14. A system for extracting a sample from a substrate, comprising:
   a sample stage for supporting the substrate;
   an ion beam source for producing a sub-micrometer diameter ion beam, the beam having a non-uniform distribution for producing sloping sidewalls on the substrate; and
   a controller programmed to control the ion beam source and the stage to carry out the method of claim 1.

15. The system of claim 14 further comprising a micromanipulator adapted to moving a probe to support and manipulate the sample.

16. A system for extracting a sample from a substrate, comprising:
   a beam source for producing a sub-micrometer diameter beam capable of milling a hole in a substrate, the beam having a non-uniform distribution for producing sloping sidewalls on the substrate; and
   a controller for controlling the movement of the beam relative to the substrate, the controller being programmed to make a series of overlapping cuts completely around the sample and moving inward toward the sample,the overlapping cuts being of increasing depth and creating a trench around the sample.

17. The system of claim 16 in which the controller is also programmed to control the beam to undercut and free the sample.

18. The system of claim 16 in which the controller is also programmed to tilt the beam or a sample stage before directing the beam to undercut and free the sample.

19. A method of extracting a microscopic sample from a substrate, the method comprising:
defining a sample section to be extracted on a substrate;
directing a charged particle beam at the substrate surface at a first angle with respect to the substrate surface and then milling the substrate surface by directing a charged particle beam along a substantially complete perimeter around the sample section in one continuous pass in order to form a trench around the sample section;
directing a charged particle beam at sample section at a second angle with respect to the substrate surface, and then milling the sample section in order to sever the base of the sample section from the substrate; and
removing the sample section from the substrate.

20. The method of claim 19 in which milling the substrate surface by directing a charged particle beam along a substantially complete perimeter around the sample section in order to form a trench around the sample section comprises:
milling the substrate surface by directing a charged particle beam in a first path along a substantially complete perimeter around the sample section in order to form a trench with sloping sidewalls around the sample section;
milling the substrate by directing a charged particle beam in a second path along a substantially complete perimeter around the sample section to enlarge the trench around the sample, the cut produced by the second path overlapping the cut produced by the first path but offset toward the sample section so that the charged particle beam directed in the second path impacts on the sloping sidewall produced by the previous beam path.

21. The method of claim 19 in which milling the substrate surface by directing a charged particle beam along a substantially complete perimeter around the sample section in order to form a trench around the sample section comprises:
milling the substrate surface by directing a charged particle beam in a first path along a substantially complete perimeter around the sample section in order to form a trench around the sample section;
enlarging said trench by directing a charged particle beam in a second path along a substantially complete perimeter around the sample section so that the beam position in the second path overlaps the beam position in the first path toward the sample section.

22. The method of claim 19 in which milling the substrate surface by directing a charged particle beam along a substantially complete perimeter around the sample section in order to form a trench around the sample section comprises:
milling the substrate surface by directing a charged particle beam in a first path along a substantially complete perimeter around the sample section in order to form a trench around the sample section, said trench having an interior sidewall closest to the sample section;
milling the substrate by directing a charged particle beam in a second path along a substantially complete perimeter around the sample section to enlarge the trench around the sample, the second path offset from the first path toward the sample section so that the charged particle beam directed in the second path impacts on the interior sidewall of said trench.

23. The method of claim 19 in which directing a charged particle beam at the substrate surface at a first angle with respect to the substrate surface comprises directing the charged particle beam at the substrate surface at a substantially normal angle with respect to the substrate surface.

24. The method of claim 23 in which said second angle is 10° to 80° with respect to the substrate surface.

25. The method of claim 19 in which said second angle is less than said first angle.

26. The method of claim 19 in which milling the substrate surface by directing a charged particle beam along a substantially complete perimeter around the sample section in order to form a trench around the sample section comprises directing the charged particle beam along a substantially complete perimeter in a series of overlapping cuts moving progressively toward the sample section in order to form a trench around the sample section.

27. The method of claim 19 in which:
directing a charged particle beam at the substrate surface comprises directing a charged particle beam at the substrate surface, said charged particle beam having a beam diameter; and
directing a charged particle beam along a substantially complete perimeter around the sample section comprises directing the charged particle beam in a series of two or more circular paths forming a perimeter around the sample section so that the beam path describes a series of concentric circles of diminishing diameter, the difference in diameter of successive circular paths being smaller than the beam diameter.

28. The method of claim 19 further comprising thinning the sample by milling with the charged particle beam.

29. The method of claim 28 in which said thinning step is performed after milling the substrate surface by directing a charged particle beam along a substantially complete perimeter around the sample section in order to form a trench around the sample section and before milling the sample section in order to sever the base of the sample section from the substrate.

30. The method of claim 19 in which directing a charged particle beam at sample section at a second angle with respect to the substrate surface, and then milling the sample section in order to sever the base of the sample section from the substrate comprises;
shaping the sample section with a charged particle beam;
tilting the sample; and
directing a charged particle beam at the sample section base in order to undercut the sample section and free the sample section from the substrate.

31. A method of extracting a microscopic sample from a substrate, comprising:
directing an ion beam at a substantially normal angle to the substrate surface along a first path substantially along a complete perimeter around a sample section to produce a trench in the substrate, wherein the ion beam is directed along the first path in one continuous pass around the sample perimeter without reversing the direction of the ion beam;
directing the ion beam at a substantially normal angle to the substrate surface along a second path. wherein the ion beam is directed along the second path in one continuous pass around the sample perimeter without reversing the direction of the ion beam, the second path overlapping but offset inwardly toward the sample section from the first path essentially along the entire perimeter to enlarge the trench around the sample; and
directing the ion beam at a substantially non-normal angle to the substrate to undercut the sample and free the sample from the substrate.

\* \* \* \* \*

UNITED STATES PATENT AND TRADEMARK OFFICE
CERTIFICATE OF CORRECTION

| | | |
|---|---|---|
| PATENT NO. | : 7,442,924 B2 | Page 1 of 1 |
| APPLICATION NO. | : 11/351315 | |
| DATED | : October 28, 2008 | |
| INVENTOR(S) | : Lucille A. Giannuzzi et al. | |

It is certified that error appears in the above-identified patent and that said Letters Patent is hereby corrected as shown below:

Title page, item [73] Assignee, change "FEI, Company" to read "FEI Company";

Drawings, Sheet 1, FIG. 1, 102 – Please change "permeter" to read "perimeter";

Drawings, Sheet 1, FIG. 1, 110 – Please change "to the a sample" to read "to the sample";

Column 2, Line 53 – Please change "FIG. 5 a cross section" to read "FIG. 5 shows a cross section";

Column 5, Line 65/66 – Please change "than the one tenth" to read "than one tenth";

Column 9, Line 52/53 – Please change "after the directing" to read "after directing";

Column 9, Line 61 – Please change "of an overlapping" to read "of and overlapping";

Column 10, Line 9 – Please change "intrest" to read "interest";

Column 10, Line 23 – Please change "in a at" to read "in at";

Column 10, Line 27 – Please change "which the cutting" to read "which cutting";

Column 10, Line 30 – Please change "which the cutting" to read "which cutting";

Column 10, Line 40 – Please change "which the cutting" to read "which cutting";

Column 11, Line 16 – Please change " at sample" to read "at the sample";

Signed and Sealed this
Fifth Day of April, 2011

David J. Kappos
*Director of the United States Patent and Trademark Office*